United States Patent [19]

Munday

[11] Patent Number: 5,720,972
[45] Date of Patent: Feb. 24, 1998

[54] DEVICE FOR ADMINISTRATION OF BENEFICIAL MATERIALS TO RUMINANTS

[75] Inventor: Rex Munday, Hamilton, New Zealand

[73] Assignee: New Zealand Pastoral Agriculture Research Institute Limited, New Zealand

[21] Appl. No.: 617,628

[22] Filed: Mar. 19, 1996

[51] Int. Cl.$^6$ .................................................. A61F 9/02
[52] U.S. Cl. ........................... 424/438; 424/464; 424/468
[58] Field of Search ................................. 424/438, 464, 424/468

[56] References Cited

U.S. PATENT DOCUMENTS

| | | | |
|---|---|---|---|
| 3,146,169 | 8/1964 | Stephenson | 167/82 |
| 3,535,419 | 10/1970 | Siegrist et al. | 424/22 |
| 4,044,119 | 8/1977 | Carlson, Jr. et al. | 424/22 |
| 4,066,754 | 1/1978 | Chou | 424/229 |
| 4,642,317 | 2/1987 | Palmquist | 514/558 |
| 4,670,248 | 6/1987 | Schricker | 424/19 |
| 4,723,958 | 2/1988 | Pope | 604/890.1 |
| 4,732,764 | 3/1988 | Hemingway et al. | 424/438 |
| 4,898,733 | 2/1990 | Deprince | 424/425 |
| 5,098,718 | 3/1992 | Ardaillon | 426/2 |
| 5,110,597 | 5/1992 | Wong | 424/438 |
| 5,110,598 | 5/1992 | Kwan | 424/438 |
| 5,429,832 | 7/1995 | Ueda | 426/96 |

FOREIGN PATENT DOCUMENTS

| | | |
|---|---|---|
| 50522/90 | 9/1990 | Australia . |
| 0062391 | 10/1982 | European Pat. Off. . |
| 220928 | 5/1987 | European Pat. Off. . |
| 236002 | 9/1987 | European Pat. Off. . |
| 204615 | 4/1986 | New Zealand . |
| 212100 | 7/1988 | New Zealand . |
| 1334658 | 10/1973 | United Kingdom . |
| 2077103 | 12/1981 | United Kingdom . |
| 2124899 | 2/1984 | United Kingdom . |
| WO 93/16708 | 9/1993 | WIPO . |

OTHER PUBLICATIONS

Poper & Baggot, "Basis for Selecting Dosage Form", and Blodinger, Formulation of Veterinary Dosage Forms, Editor J. Blodinger, pp. 45–49, 140–143, 172 and 173 (1983).
Toxinology & Food Safety Research Report (Dec. 1995).
*The Zinc Bolus*, AgResearch (published Jul. 18, 1994).
Rural News (Dec. 6, 1993).
*Zinc for sheep trialled*, NZ Herald (published Nov. 11, 1993).
*Slow release zinc capsule offers protection*, The New Zealand Sheep Farmer (published Oct. 1993).
Gordon Levet, *Zinc bolus may deliver facial eczema control*, Supplement New Zealand Farmer (Spring 1994).
*Slow release bolus major FE weapon*, The New Zealand Farmer (Sep. 28, 1994).

*Primary Examiner*—D. Gabrielle Phelan
*Attorney, Agent, or Firm*—Burns, Doane, Swecker & Mathis, LLP

[57] ABSTRACT

The invention described is a bolus for the controlled release of a beneficial agent in the rumen of a ruminant animal. The bolus consists in a core containing a binder, solubilising agent, the beneficial agent to be released and, when required, a densifier. The core is coated with a wax coating, preferably with an opening exposing a small part of the core to rumen juices. The core is gradually dissolved releasing the beneficial agent. As the core dissolves the wax coating erodes until the bolus disappears completely.

25 Claims, 3 Drawing Sheets

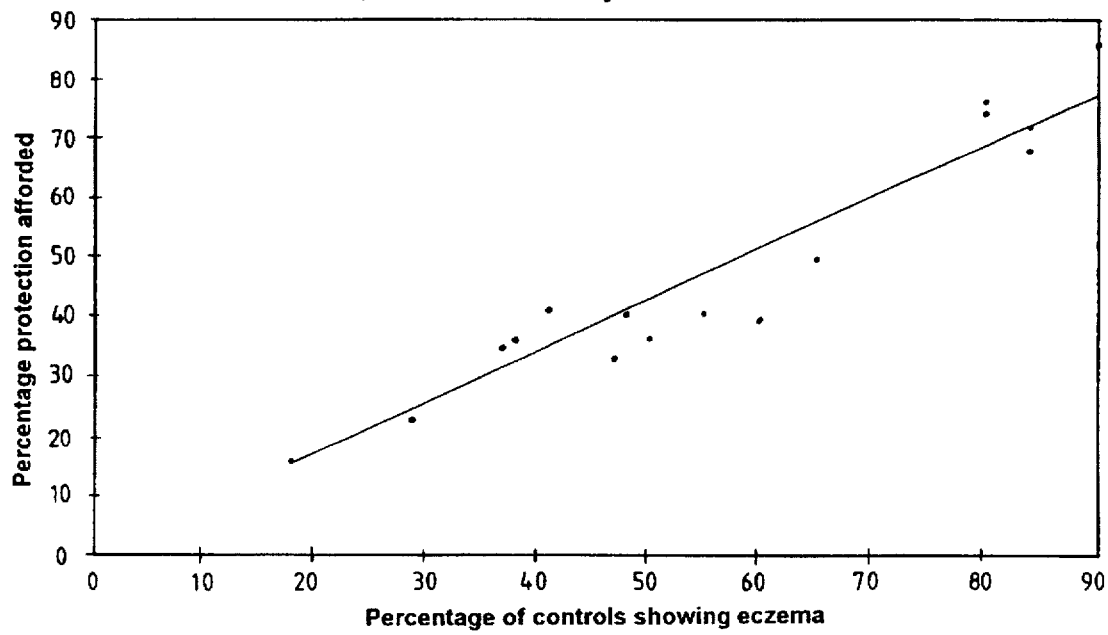
FIG. 7  Plot of percentage of controls showing eczema against percentage protection afforded by the 4-week device
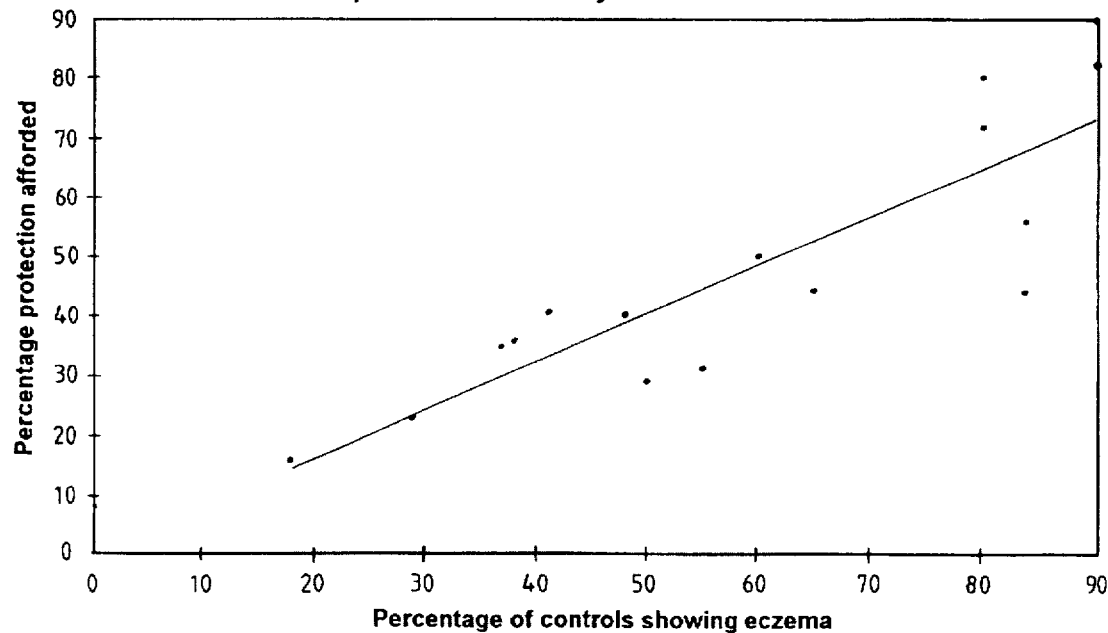
FIG. 8  Plot of percentage of controls showing eczema against percentage protection afforded by the 6-week device 5,720,972

DEVICE FOR ADMINISTRATION OF BENEFICIAL MATERIALS TO RUMINANTS

TECHNICAL FIELD

This invention relates to a controlled release device. More particularly, it relates to a bolus for releasing beneficial substances into the rumens of ruminants.

BACKGROUND ART

Slow release devices or boluses are well known in the art. In GB 2, 122,086 there is described a bolus having a compressed core containing an active ingredient and a skin of brittle material. The core is exposed to the rumen fluids and gradually disintegrates. The brittle skin which is supported by the core breaks away as the support disappears. The core is made of dry mixed materials which are compressed together. It is difficult to compress a core of uniform density. If the core is not homogeneous in its density there is an uneven distribution of material during disintegration which can be a disadvantage if the beneficial material has to be dispensed at particular rates.

U.S. Pat. No. 3,535,419 describes a bolus having three separate components:

a) one or more highly water insoluble materials such as a solid wax, fat, oil, fatty acid amide, ester or alcohol or polymer;

b) a high density non-toxic metal derivative; and c) a therapeutic agent.

Its method of operation is by disintegration of the composition and leaching out of the active ingredient. The rate of dissolution is determined by the degree of compression and the surface area which will reduce over time causing a reducing rather than constant delivery rate.

It is an object of the present invention to go some way towards overcoming the disadvantages of the prior art or at least to offer the public a useful choice.

DISCLOSURE OF THE INVENTION

Accordingly, the invention may be said broadly to consist in a bolus which comprises:

i) a core comprising a substantially homogeneous mixture of:

a) a water insoluble physiologically acceptable binder comprising wax, fat, oil, fatty acid, fatty acid ester, fatty acid amide, fatty acid alcohol or the like organic compound having a melting point sufficiently above the internal temperature of the animal intended to ingest the bolus so as not to allow the bolus to melt after ingestion;

b) a physiologically acceptable solubilising agent;

c) a beneficial agent; and d) where required, a physiologically acceptable inert densifier of sufficient density and in sufficient quantities to give the bolus a minimum density of 1.5 g/cm$^3$; and ii) a coating of a physiologically acceptable degradable material over substantially all of the surface of the core but leaving exposed a core portion whereby in use liquid in the rumen will dissolve said core allowing release of the beneficial agent into the rumen.

Preferably said degradable material is wax.

Alternatively said degradable material is a substrate coated with a waterproofing material.

Preferably said waterproofing material is wax.

Alternatively said waterproofing material is polyurethane.

Preferably said substrate is paper.

Preferably the melting point of said binder is at least 50° C.

Preferably said binder comprises a fatty acid ester.

Preferably said fatty acid ester is glycerol monostearate.

Preferably said solubilising agent is polyethylene glycol stearate.

Alternatively, said solubilising agent is a sodium salt of a long chain fatty acid.

Preferably said beneficial agent is a nutrient.

Alternatively said beneficial agent is a growth promotant.

Alternatively, said beneficial agent is a therapeutic substance or substances.

Alternatively, said beneficial agent is a mixture of a nutrient and one or more therapeutic substances.

Preferably said beneficial agent is zinc oxide.

Preferably said densifier is iron powder, barium sulphate or iron oxide.

Preferably said bolus is in the shape of a cylinder which is closed at one end and open at the other.

Preferably said closed end is hemispherical in shape.

In an alternative construction, said core is cylindrical and consists in alternating cylindrical layers, each alternate layer containing all of the ingredients of the core except the beneficial agent whereby the beneficial agent is released in separate doses.

Preferably said bolus is as herein described with reference to the drawings.

In another embodiment the invention may be said broadly to consist in a method of making a bolus which comprises:

a) melting a mixture of a water insoluble physiologically acceptable binder comprising wax, fat, oil, fatty acid, fatty acid ester, fatty acid amide, fatty acid alcohol or the like organic compound having a melting point sufficiently above the internal temperature of the animal intended to ingest the bolus so as not to allow the bolus to melt after ingestion; a physiologically acceptable solubilising agent; a beneficial agent; and where required, sufficient physiologically acceptable inert filler material of sufficient density to give the bolus a minimum density of 1.5 g/cm$^3$;

b) mixing said mixture until it is substantially homogeneous;

c) dividing said substantially homogeneous mixture into predetermined dosages; and d) coating said dosages with a physiologically acceptable degradable material.

Preferably in said step (c) said substantially homogeneous mixture is extruded and cut into predetermined dosage lengths.

Alternatively said step (c) comprises pouring said substantially homogeneous mixture in the form of a melt into a mould and allowing it to solidify.

In another embodiment said step (a) is carried out so that the said mixture is in two parts and said beneficial agent is included in one only of said parts, and said step (c) comprises arranging said two parts in alternating layers of inert core and core containing beneficial agent.

In another alternative said step (d) comprises forming said mould as a substrate coated with waterproof material prior to pouring said melt thereinto said substrate forming said coating.

In another alternative process said binder and said solubilising agent are dissolved in a physiologically acceptable solvent and said solvent is allowed to evaporate from said dosages into which said mixture has been divided prior to said coating step.

Preferably said coating step comprises coating all but a small area of each said dosage length.

Preferably each said dosage is in the form of a cylinder and said coating step comprises coating all but one end thereof.

The invention consists in the foregoing and also envisages constructions of which the following gives examples.

BRIEF DESCRIPTION OF THE DRAWINGS

The invention may also be understood by having reference to the accompanying drawings in which:

FIG. 7 is a plot of percentage of controls showing facial eczema against percentage protection afforded by a four week bolus.

FIG. 8 is a plot of percentage of controls showing facial eczema against percentage protection afforded by a six week bolus.

MODES OF CARRYING OUT THE INVENTION

Figure 1A:
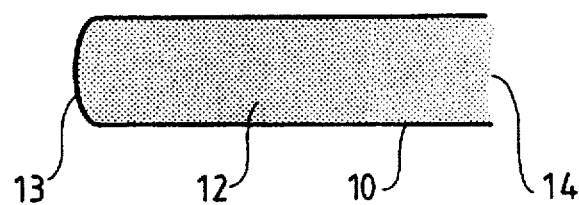
FIGS. 1A, 1B and 1C are cross-sectional elevations of a first embodiment of a bolus according to the invention showing the mode of release of beneficial agent.
Figure 1B:
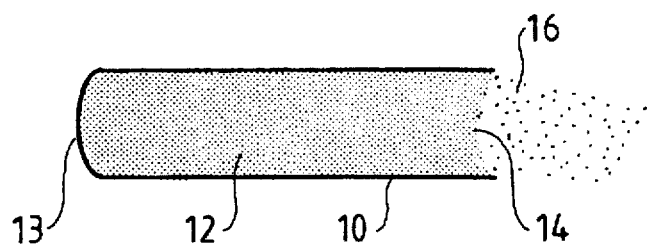
Figure 1C:
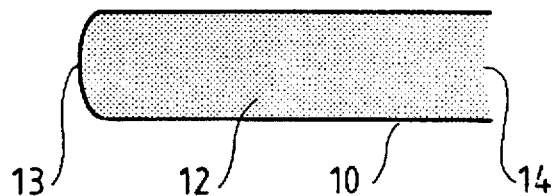

The bolus illustrated in FIG. 1 comprises a core 12 coated by a wax coating 10. The coating 10 is closed at one end 13 and open at the other 14. The closed end 13 may be hemispherical in shape or have a substantially flat bottom as illustrated. The open end 14 of the wax coating allows the core 12 to be exposed to the juices in the rumen. As illustrated in FIG. 1B, the juices in the rumen gradually dissolve the core 12 releasing particles 16 of active agent. As the wax coating 10 erodes at the open end 14 the core 12 is dissolved so that the bolus as illustrated in FIG. 1C becomes progressively shorter until it has disintegrated completely.

Figure 2:
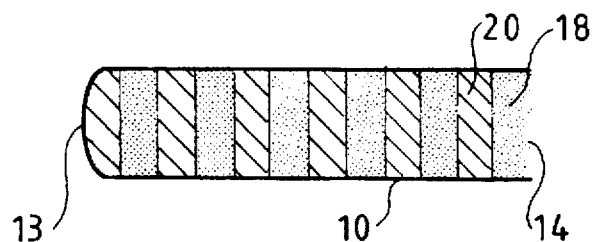
FIG. 2 is a cross-sectional elevation of a second embodiment of a bolus according to the invention showing alternative active and inert core layers.

In FIG. 2 the bolus is identical to the one illustrated in FIG. 1A except that instead of being provided with a homogeneous core it is provided with a core consisting of alternating layers 18 and 20. Layer 18 consists of all of the filler materials and includes the beneficial agent as described below. Layer 20 contains only the filler materials and no beneficial agent. The bolus illustrated in FIG. 2 is gradually dissolved and eroded in the same way as that illustrated in FIGS. 1A to 1C but the beneficial ingredient is leached out at spaced intervals. Such a bolus would be used where beneficial agents such as medicaments are to be administered in pulsed dosages. The length of time between administration of doses can be controlled by the thickness of the inert layers 20.

Figure 3:
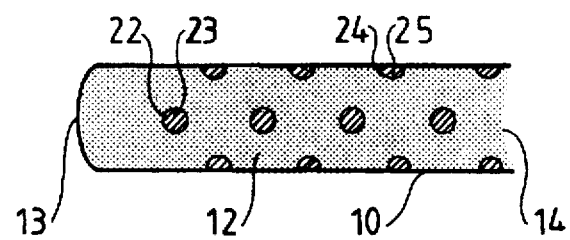
FIG. 3 is a cross-sectional elevation of another embodiment of a bolus according to the invention in which beneficial agent is stored in transverse cavities or grooves in the core.

The bolus in FIG. 3 is intended to dispense beneficial agents in pulsed dosages as well. The core 12 contains all of the inert ingredients, that is the binding agent, solubilising agent and densifier if necessary. The core 12 is provided with either bores 22 extending transversely through the core, or circumferential rings or grooves 24. The bores 22 or grooves 24 contain the beneficial agents 23 or 25, respectively, in a concentrated form. The core and bore or grooves are coated with wax in the same manner as for the other embodiments. As the wax coating erodes the beneficial ingredient 23 or 25 is released in dosage pulses as it is exposed to the rumen juices.

Figure 4:
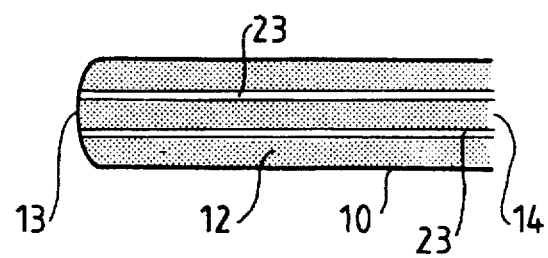
FIG. 4 is an elevation of another embodiment of a bolus according to the invention in which beneficial agent is present in longitudinal bores in the core surface just below the outer coating.

As shown in FIG. 4 beneficial agent may also be placed in longitudinal grooves 23 cut in the surface of core 12. The filled grooves are then coated with wax coating 10 along with the rest of core 12.

Figure 5:
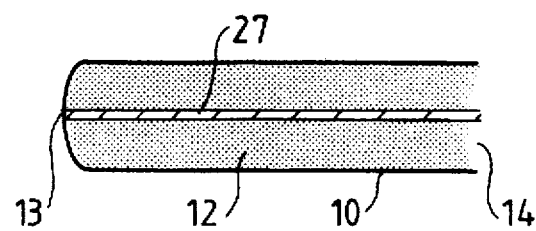
FIG. 5 is a cross-sectional elevation of another embodiment of a bolus according to the invention in which beneficial agent is present in a longitudinal bore within the core of the bolus.

As shown in FIG. 5 a beneficial agent may be placed in longitudinal bore 27 as well.

Figure 6A:
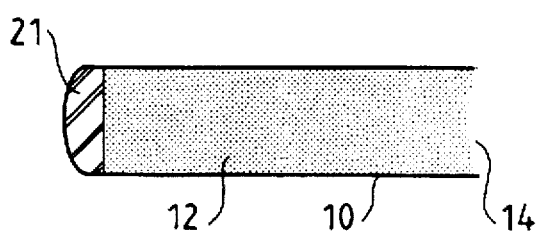
FIG. 6A is a longitudinal section of a further embodiment of the invention.

The bolus illustrated in FIG. 6A is intended for uniform controlled release of a therapeutic. It is essentially the same shape as the other embodiments i.e. cylindrical with one closed end which is hemispherical in shape. The open end 14 is similar to and has the same function as the open ends 14 of the other embodiments.

The coating 10 comprises a substrate, preferably of paper, which has been coated or impregnated with waterproofing material. A densifier, 21 such as iron powder, may be packed at the closed end.

Figure 6B:
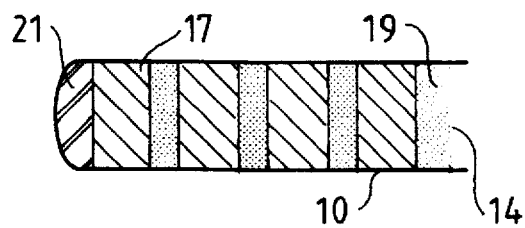
FIG. 6B is a longitudinal section of an alternative to the embodiment shown in FIG. 6A.

The core of the embodiment shown in FIG. 6B allows for pulsed delivery of beneficial material.

The core layers 17 contain the same core material as the other embodiments but no beneficial material. The layers 19 contain core material and beneficial material. This allows for the pulsed release of beneficial material according to the treatment or nutritional regime. In another embodiment, layers 17 and 19 contain different beneficial materials. In this embodiment there is a densifier 21 at the closed end of the bolus.

In an alternative embodiment the densifier is distributed uniformly throughout the core layers 17 and 18. The densifier will be concentrated at the closed end in boluses where the beneficial material is of a very low density and it may be impractical to distribute the densifier throughout the composition.

PRODUCTION METHOD

The cores according to the invention may be produced by either extrusion or by pouring and allowing either the melted binding agent to solidify or allowing solvent to evaporate as the case may be.

All of the ingredients except the wax outer coating are mixed together. Where no solvent is used the mixture is heated to melt the binding agent and then stirred into a substantially homogeneous mixture. If a moulding method is used the mixture is poured into moulds having the shape of the cores of the drawings and allowed to cool. The cores are then released from the mould and coated with the wax either by dipping or pouring the wax over the core. If a solvent is used the binding agent is dissolved in the solvent rather than being melted and the solvent is allowed to evaporate.

When an extruder is used the mixture of ingredients is allowed to cool or the solvent allowed to evaporate into the form of a semi-solid paste. The extruded material is cut into appropriate dosage lengths. When a core of the construction shown in FIG. 2 is to be made a pair of extruders are run next to one another. One extruded mixture contains no beneficial agent. The other one contains the beneficial agent in the desired dosage form. The extrusions are then cut into relatively short lengths as illustrated in FIG. 2 and placed together in alternating active and inert layers and coated as described above.

In one alternative a dual channel extruder can be equipped with a valve alternating extrusion of slugs of material from one channel or the other.

When producing the core illustrated in FIG. 3 an extrusion containing all but the beneficial ingredient and cut to lengths is then drilled by a series of drills operating in parallel or else grooved using a router and rotating device to produce either the bores 22 through the core or the grooves 24 around the core. Beneficial agent 23 in a substantially melted form is then poured into the bores 22 and the core is then coated with waxes described above. In order to keep the active ingredient within the core the drills producing bores 22 are positioned so as to not pass completely through the bottom of the core beneath them. When grooves 24 are used beneficial ingredient in the form of a paste 23 is extruded into the grooves and the core coated in the usual way. Longitudinal grooves 23 and longitudinal bores 27 (see FIGS. 4 and 5) are formed and filled with beneficial agent in a similar manner.

The bolus as illustrated in FIG. 6A is made by the following moulding technique. An outer coating 10 is made from a substrate such as paper which has been coated or impregnated with a waterproofing material such as wax or polyurethane. This then forms the mould. When employed, the densifier 21 (which can be any material of sufficient density which is physiologically acceptable) is inserted, and the molten core material is placed in the mould until the latter is full.

The bolus as shown in FIG. 6B is intended for pulsed release of beneficial material. The mould is the same as that described for the previous embodiment. The core ingredients are mixed in two separate batches, one of which contains a beneficial material and one of which does not. Each of the two mixtures are melted. The melted The melted mixture not containing beneficial material is placed in the mould first as the lower most layer 17. The next layer 19 is a layer of melted binder with beneficial material. The alternating layers then continue until the mould has been completely filled. It is also possible to use the same manufacturing technique to be able to deliver alternating beneficial ingredients. In such an embodiment one beneficial ingredient would be in one layer 19 and another in a layer 17. Such a bolus could be used in administering a combined course of therapeutics or a combined course of nutritional materials.

The substrate used to form the mould is preferably paper but alternative thin layer substrates which erode in the rumen of an animal are acceptable. The waterproofing agent may be wax, polyurethane or any other physiologically acceptable waterproofing agent.

ALTERNATIVE FORMULATIONS

The binding agent for the core can be any physiologically acceptable water insoluble component which can be formed into a substantially homogeneous mixture with the solubilising agent, the beneficial agent and the densifying agent. Most preferably the binding agent will be one which can be melted at temperatures not deleterious to the other components or one which is soluble in solvents which can be evaporated to allow the core to solidify. The melting point of the binder should also be sufficiently above the internal body temperature of the animal ingesting it so that it does not melt in situ. For most animal applications the appropriate melting point is at least 50° C. Any solvent used would have to be physiologically acceptable to the animal being fed the bolus. Suitable binding agents are those exemplified in U.S. Pat. No. 3,535,419. We have found that glycerol monostearate is a particularly suitable binding agent.

The solubilising agent works in conjunction with the binding agent in the rumen environment in a manner not completely understood. However, it is believed that the solubilising agent together with the gastric juices gradually dissolve the binding agent in the core.

In the embodiment described in the following example the beneficial agent is zinc oxide. Zinc oxide has a sufficient density that it is not necessary to include a high density inert material to weight the bolus down so that it is not disgorged from the rumen.

Persons skilled in the art will be aware of other beneficial ingredients which can be administered through use of this bolus. This can include additional nutrients where these are necessary and other therapeutic agents for the treatment of parasites, diseases or other afflictions of ruminants.

In order to avoid the bolus being regurgitated from the rumen, it preferably has a minimum density of 1.5 g/cm$^3$. More preferably the density is 2.5 g/cm$^3$. With many therapeutic agents other than zinc oxide it will be necessary to include densifying substances. These should be inert and physiologically acceptable to the animal intended to ingest the bolus. The density of the densifier should be sufficient to give the desired minimum density to the entire bolus.

A wide variety of waxes may be used. A mixture of paraffin wax and of carnauba wax or a mixture of bees wax and carnauba wax have been found to be successful. The wax used will need to be physiologically acceptable to the animal o intended to ingest it and be of such a composition that it erodes at the open end under the conditions within the rumen.

EXAMPLE 1

Preparation of a bolus containing zinc oxide

A mixture containing 83.5% zinc oxide and 16.5% glycerol monostearate was melted and mixed. The glycerol monostearate contained 75 to 90% EMULDAN HS40 (a trade name for glycerol monostearate non-sell-emulsifying) and 10 to 25% LIPOMULSE 165 (a trade name for glycerol monostearate self-emulsifying, which is a blend of glycerol monostearate and polyethylene glycol monostearate). The mixture was then extruded and core lengths cut to predetermined dosage lengths and coated with a wax. The wax consisted of 25% carnauba wax and 75% paraffin wax. EMULDAN HS40 was obtained from Grindsted Products A/S of Brabrand, Denmark and LIPOMULSE 165 from Lipo Chemicals Inc, of Paterson, N.J., USA. All of the percentages are by weight of the core mixture or of the wax coating.

EXAMPLE 2

Boluses with Different Release Times (a) Four Week Release Time

A bolus was prepared as in example 1. The glycerol monostearate comprised 80% non-self-emulsifying glycerol monostearate (EMULDAN HS40) and 20% self-emulsifying glycerol monostearate (LIPOMULSE 165).

It was found that a bolus containing 43 gm of zinc oxide was fully dissolved and eroded in sheep of weight ranges of 20 to 40 kg on average in about four weeks.

(b) Six Week Release Time

A bolus was prepared as in example 1. The glycerol monostearate comprised 85% non-self-emulsifying glycerol monostearate (EMULDAN HS40) and 15% self-emulsifying glycerol monostearate (LIPOMULSE 165).

It was found that a bolus containing 43 gm of zinc oxide was fully dissolved and eroded in sheep of weight ranges of 20 to 40 kg on average in about 6 weeks.

EXAMPLE 3

Manufacture of Bolus in Degradable Mould

A paper mould, 100 mm long and cylindrical in shape with an open end and a hemispherical closed end, was coated with polyurethane over the whole of the outside surface. The polyurethane was applied by painting on a commercially available solvent-based polyurethane. The coated polyurethane mould was left to dry for 24 hours. It was then filled up to the open end with a melted core mixture containing 85% barium sulphate and 15% of glycerol monostearate (sold under the trade name EMULDAN HB40M). Care was taken not to trap any air within the mould. The device was then allowed to cool and the core solidified. The device was placed in the rumen of a fistulated cow. It was fully eroded over a period of 11 weeks.

EXAMPLE 4

Field Trials

Boluses prepared as in examples 1 or 2 containing a core comprising 83.5% zinc oxide and 16.5% glycerol monostearate, were administered to lambs. One released the zinc over a 4-week period, the other over 6 weeks. These devices were tested for their ability to prevent facial eczema (FE) in lambs on farms in Northland, Auckland, Waikato and Wanganui in New Zealand during the 1994 FE season. (February to March 1994).

Groups of approximately 50 lambs on 26 farms in these regions received one or other of the devices, which were renewed every 4 to 6 weeks until the end of the FE season. On farms where precautions against FE were normally taken, a control group was left untreated so that the protective effect of the devices could be assessed. On properties where no precautions were taken, a random-chosen group of lambs was used as control.

Blood samples were regularly taken from the control group for assay of γ-glutamyl transferase (GGT) activity, a measure of the liver damage caused by FE. When significant liver damage was detected in the control group, all the lambs were bled, and the severity of the liver damage categorised according to GGT activity (measured in international units) as follows:

| | |
|---|---|
| >55 | No eczema |
| 55–150 | Mild eczema |
| 151–330 | Moderate eczema |
| >330 | Severe eczema |

Facial eczema occurred on 15 of the farms under study. Some farms, were severely affected by FE during 1994, with more than 80% of the unprotected control lambs showing liver damage. On two farms, the outbreak was very prolonged, and a second blood sample taken in May showed a continuing severe challenge in the control lambs. Excellent protection was given by both devices, with less than 10% of the animals showing any signs of liver damage over the whole of the observation period. Good protection was also seen on the two other most affected farms, with both the incidence and severity of liver damage being greatly reduced.

A less severe challenge was seen on seven farms with between 40 and 65% of the control animals being affected. Again, excellent protection was given by the intraruminal devices, with the incidence of eczema being generally less than 20% and then only in the "mild" category.

Comparatively little eczema was recorded on the remaining four farms with an 18–38% incidence of liver damage. On these farms, the devices gave almost complete protection.

On one of the severely affected farms, lambs other than the controls were given zinc oxide by drench at fortnightly intervals throughout the FE season. A sample of these animals was bled on 11 May for comparison with the control lambs and those given the intraruminal devices. These data show that fortnightly dosing does decrease the incidence of facial eczema (90% in the control compared with 64% in the zinc-dosed animals) but it is nowhere near as effective as the zinc intraruminal devices, both of which reduced the incidence of eczema to less than 10%.

STATISTICAL ANALYSES

In the first analyses, the animals were divided into two groups—those that showed no eczema and those showing some sign of the disease, irrespective of its severity.

The overall means percentage of animals showing no eczema are shown in Table 1.

TABLE 1

Overall mean percentage of animals showing no eczema - all trials

| | Mean percent without eczema |
|---|---|
| Control | 41.4 ± 5.5 |
| 4-week device | 88.8 ± 3.0* |
| 6-week device | 91.4 ± 1.6* |

*Significantly different from the control value, $P < 0.001$.

In order to establish the overall efficacy of the devices, the data from each farm was analysed by plotting the percentage of controls showing eczema against the percentage protection afforded, defined as the percentage of animals in the treated group without eczema less the percentage of animals in the control group without eczema.

These plots are shown in FIGS. 6 and 7 for the 4- and 6-week devices respectively. As expected, the lines pass through the origin in both cases; if there is no eczema, there can be no protection. The points arc fitted to a straight line; from the slopes of these lines it can be predicted that 86±3% of animals in a flock would be protected by the 4-week device and 81±4% by the 6-week device. In simple terms, this indicates that if 100 control sheep were grazed on toxic pasture and 80 were affected, by a greater or lesser degree, with eczema, on average, only 11 of animals treated with the 4-week device and 15 of those treated with the 6-week device would show any sign of eczema.

Such an analysis does not, however, take into account the severity of the disease. A minor amount of liver damage is of little consequence in practical terms, and protection against moderate or severe eczema is of paramount importance. The data were therefore re-analysed, eliminating animals which suffered only mild eczema. From this analysis, it is predicted that 95±1% of animals in a flock would be protected from moderate or severe eczema by the 4-week device and 89±3% of animals by the 6-week device.

The results from these experiments show that the intraruminal devices consistently decrease the incidence and severity of facial eczema in grazing lambs under normal farming conditions, even after severe and prolonged challenge.

Although this invention has been described in relation to the controlled release of zinc to control facial eczema it will be appreciated by those skilled in the art that many other beneficial agents may be released by use of the bolus of this invention.

It will also be appreciated that the rate and timing of release is controlled by both the configuration of beneficial agent within the core and by the solubility of the core. The solubility can be altered by use of a greater or lesser proportion of solubilising agent.

I claim:

1. A bolus which provides for the release of a therapeutic agent in the rumen of an animal which consists essentially of the following:
   (i) a core structure which erodes at a uniform rate in the rumen of an animal which comprises a mixture of:
      (a) a water-insoluble physiologically acceptable binder material selected from the group consisting of fatty acids, waxes, fats, oils, fatty acid esters, fatty acid amides, and fatty acid alcohols, wherein such binder material possesses a melting point above the internal temperature of the rumen of the animal which will ingest the bolus and therefore not melt upon ingestion;
      (b) a physiologically acceptable solubilizing agent;
      (c) at least one beneficial agent; and
      (d) if necessary, a physiologically acceptable densifier which is contained in a sufficient amount and having a sufficient density to provide for a bolus having a minimum density of 1.5 g/cm$^2$; and wherein such core structure is produced by mixing the materials together under conditions which result in a substantially homogeneous mixture which may be extruded or molded into a desired shape; and
   (ii) which core structure is coated with a physiologically acceptable material which erodes in the rumen, and which coating material covers substantially all the surface of the core structure except for a small exposed core portion, thereby providing for simultaneous erosion of the core structure and of the coating material in the rumen, and thereby also providing for controlled release of the beneficial agent in the rumen.

2. The bolus according to claim 1, wherein said erodible material is a wax.

3. The bolus according to claim 1, wherein said degradable material is a substrate which is coated with a waterproof material.

4. The bolus according to claim 3, wherein said substrate is paper and said waterproof material is selected from the group consisting of wax and polyurethane.

5. The bolus according to claim 1, wherein the melting point of said binder is at least 50° C.

6. The bolus according to claim 1, wherein said binder is a fatty acid ester.

7. The bolus according to claim 6, wherein said fatty acid ester is glycerol monostearate.

8. The bolus according to claim 1, wherein said solubilizing agent is polyethylene glycol stearate.

9. The bolus according to claim 1, wherein said solubilizing agent is a sodium fatty acid salt.

10. The bolus according to claim 1, wherein said beneficial agent is a nutrient.

11. The bolus according to claim 1, wherein said beneficial agent is zinc oxide.

12. The bolus according to claim 1, wherein said beneficial agent promotes growth.

13. The bolus according to claim 1, which comprises both a nutrient and a therapeutic substance as said at least one beneficial agent.

14. The bolus according to claim 1, wherein said densifier is selected from the group consisting of iron powder, barium sulfate and iron oxide.

15. The bolus according to claim 1, which is in the shape of a cylinder closed at one end and open at the other.

16. The bolus according to claim 15, wherein said closed end is hemispherical in shape.

17. The bolus according to claim 1, wherein said core is cylindrical and consists of alternating cylindrical layers, each alternate layer containing all of the ingredients of the core except the beneficial agent thereby providing for the release of the beneficial agent in separate doses.

18. A method for producing a bolus which provides for the release of at least one beneficial agent in the rumen of an animal which method comprises the following steps:
   (a) providing a melt comprising a mixture of a water-insoluble physiologically acceptable binder material selected from the group consisting of waxes, fats, oils, fatty acids, fatty acid esters, fatty acid amides, and fatty acid alcohols which possess a melting point sufficiently above the internal temperature of the animal which is intended to ingest the bolus such that the bolus does not melt upon ingestion; a physiologically acceptable solubilizing agent; at least one beneficial agent; and if necessary, a sufficient amount of a physiologically acceptable inert material having a sufficient density to provide a bolus having a minimum density of 1.5 g/cm$^3$;
   (b) mixing said mixture until it is substantially homogeneous;
   (c) dividing said substantially homogeneous mixture into predetermined dosages; and
   (d) coating each of said dosages with a physiologically acceptable material, which physiologically acceptable material erodes in the rumen, and wherein such coating covers substantially all the surface of the dosage except for a small exposed portion thereby providing for simultaneous erosion of the core structure and of the coating material surrounding the core structure in the rumen, and the controlled release of the at least one beneficial agent in the rumen.

19. The method according to claim 18, wherein said homogeneous mixture is extruded and cut into predetermined dosage lengths.

20. The method according to claim 18, wherein step (c) comprises pouring said substantially homogeneous mixture in the form of a melt into a mold and allowing it to solidify.

21. The method according to claim 18, wherein step (a) is effected such that said mixture is comprised of two parts and said at least one beneficial agent is contained in only one of said parts, and said step (c) comprises arranging said two parts in alternate layers of inert core and core containing beneficial agent.

22. The method according to claim 20, wherein said step (d) comprises forming said mold as a substrate coated with a waterproof material prior to pouring said melt therein, said substrate forming said coating.

23. The method according to claim 18, wherein said binder and said solubilizing agent are dissolved in a physiologically acceptable solvent and said solvent is permitted to evaporate from said dosages prior to said coating step.

24. The method according to claim 18, wherein said dosage is in the form of a cylinder and said coating step comprises coating all but one end thereof.

25. A method of administering a therapeutic or beneficial agent to a ruminant animal which comprises feeding said animal a bolus according to claim 1.

* * * * *